US005736313A

United States Patent [19]

Spargo et al.

[11] Patent Number: 5,736,313

[45] Date of Patent: Apr. 7, 1998

[54] METHOD OF LYOPHILIZING PLATELETS BY INCUBATION WITH HIGH CARBOHYDRATE CONCENTRATIONS AND SUPERCOOLING PRIOR TO FREEZING

[75] Inventors: Barry J. Spargo, Baltimore; Alan S. Rudolph, Potomac, both of Md.; Richard G. Emler, Iowa City, Iowa; Thomas R. Groel, II, Manassas, Va.

[73] Assignee: The United States of America as represented by the Secretary of the Navy, Washington, D.C.

[21] Appl. No.: 546,464

[22] Filed: Oct. 20, 1995

[51] Int. Cl.$^6$ .............................. A01N 1/02; A01N 63/00
[52] U.S. Cl. ............................................ 435/2; 424/93.72
[58] Field of Search ........................... 435/2; 424/93.72

[56] References Cited

U.S. PATENT DOCUMENTS

| | | | |
|---|---|---|---|
| 3,932,943 | 1/1976 | Briggs et al. | 34/5 |
| 4,287,087 | 9/1981 | Brinkhous et al. | 252/408 |
| 4,585,735 | 4/1986 | Meryman et al. | 435/2 |
| 4,874,690 | 10/1989 | Goodrich, Jr. et al. | 435/2 |
| 4,994,367 | 2/1991 | Bode et al. | 435/2 |
| 5,043,261 | 8/1991 | Goodrich, Jr. et al. | 435/2 |
| 5,045,446 | 9/1991 | Goodrich, Jr. et al. | 435/2 |
| 5,059,518 | 10/1991 | Kortwright et al. | 435/6 |
| 5,153,004 | 10/1992 | Goodrich, Jr. et al. | 424/533 |
| 5,171,661 | 12/1992 | Goodrich, Jr. et al. | 435/2 |
| 5,178,884 | 1/1993 | Goodrich et al. | 424/533 |
| 5,213,814 | 5/1993 | Goodrich, Jr. et al. | 424/532 |
| 5,250,303 | 10/1993 | Meryman et al. | 435/2 |

OTHER PUBLICATIONS

Holme et al., Improved maintenance of platelet in vivo viability during storage when using a synthetic medium with inhibitors. J. Lab. Clin. Med. 119:144–150, 1989.

Bode et al., Sustained elevation of intracellular cyclic 3'-4' adenosine monophosphate is necessary for preservation of platelet integrity during long-term storage at 22° C. Blood 83:1235–1243, 1994.

Read et al., Preservation of hemostatic and structural properties of rehydrated lyophilized platelets: potential for long-term storage of dried platelets for transfusion. Proc. Natl. Acad. Sci. USA 92:397–401, 1995.

Bode and Miller, The use of thrombin inhibitors and aprotinin in the preservation of platelets stored for transfusion. J. Lab. Clin. Med. 113: 753–758, 1989.

Lioneti FJ et al, Cryobiology 13:489–499 (1976).

*Primary Examiner*—Sandra E. Saucier
*Attorney, Agent, or Firm*—Thomas E. McDonnell; Barry A. Edelberg

[57] ABSTRACT

A process and medium are disclosed for the lyophilization of platelets. During lyophilization, carbohydrate-load platelets are supercooled while suspended in a buffer solution including a biocompatible polymer that serves to preserve the structure of the platelets. The supercooled platelets are then frozen at a temperature below the glass transition temperature of the suspension. A vacuum is placed on the frozen suspension to remove most of the water therefrom. Then, the temperature of the platelets is increased to the supercooled temperature while the vacuum is maintained. After being sealed under vacuum, the lyophilized platelets may be reconstituted to form viable, transfusable platelets. The reconstituted platelets have a high aggregation index, retain normal agglutination and degranulation capability, and are able to participate in clot formation.

16 Claims, 1 Drawing Sheet

METHOD OF LYOPHILIZING PLATELETS BY INCUBATION WITH HIGH CARBOHYDRATE CONCENTRATIONS AND SUPERCOOLING PRIOR TO FREEZING

BACKGROUND OF THE INVENTION

1. Field of the Invention

The present invention relates to the preservation of blood platelets. Specifically, the present invention concerns a method and solution for freeze-drying platelets.

2. Description of the Background Art

Platelets are single cells in the circulation directly involved in the coagulation process. In cases where damage to vascular tissue occurs, platelets act by adherence to collagen and basement membranes which have been exposed. Following adherence, there is a release of constituents from intracellular granules. These compounds promote vasoconstriction, and aggregation of other platelets in the area of damage. The results of this behavior are a stimulation of coagulation and an arresting of bleeding in damaged blood vessels.

Platelets are formed from megakaryocytes in the bone marrow. They are shaped like discs and range from 5 $mm^3$ to 12 $mm^3$ in size with an average of 7.1–7.5 $mm^3$. The membrane is composed of proteins and phospholipids, beneath which are submembranous filament of actomyosin. They enter the circulation by fragmentation of the megakaryocyte and survive in the circulation for about ten days. Most remain in the general circulation, but about one third remain as a pool in the spleen.

Platelet transfusion has become an important aspect of transfusion medicine. A variety of injuries calls for the transfusion of platelets, most cases involving excessive bleeding. However, an effective inventory of platelet concentrates has been difficult to obtain due to the rapid loss of platelet function during storage. Platelets are generally storable after separation from whole blood which has been drawn into citrate-dextrose-phosphate-adenine (CPDA-1). This separation must normally be performed within six hours of collection with the blood at room temperature (22° C.). The platelets are normally stored as concentrates in containers composed of polyoefin for periods up to 5–7 days at room temperature. The risks of bacterial growth in solutions stored at room temperature for this period limits the time during which platelets may be used for transfusion to five days, as established by the FDA. Storage in liquid form at temperatures below room temperature leads to substantial loss in platelet functions, such as platelet aggregation and release responses, membrane glycoprotein expression, etc. Solutions such as DMSO devised for freezing platelets pose problems due to toxicity and the poor ability of the platelets to withstand freezing.

Lyophilization of platelets provides an alternative preservation method. Lyophilized cells can be stored at room temperature for an extended period of time and easily reconstituted for use. Further, lyophilization improves both shelf life and transportation logistics. However, in order to fulfill their normal coagulation function after reconstitution, it is crucial to maintain normal intact membranes, functional enzymes, and preserve aggregation, release, and phagocytosis responses, i.e. produce viable platelets. Viable platelets can be characterized by one or more of the preceding variables. Therefore, there is a dire need for a method for lyophilizing or freeze-drying platelets which will provide viable and transfusable cells after reconstitution.

SUMMARY OF THE INVENTION

Accordingly, it is an object of the present invention to provide a process for the lyophilization of platelets.

It is another object of the present invention to provide a composition for the lyophilization of platelets.

It is yet another object of the present invention to provide a composition of freeze-dried platelets which have been freeze-dried according to the process of the present invention which, when reconstituted, have a high aggregation index, and are transfusably useful.

The present invention provides a process and composition for freeze-drying platelets. The process of the present invention allows for significantly reduced residual water content over previously patented processes with a potential for significantly increased shelf life of the freeze-dried product. Further, the present process reduces the need for post-processing removal of cryoprotectant. Most importantly, the composition of the present invention provides freeze-dried platelets which, when reconstituted, are viable and have a high aggregation index, are capable of degranulation, and participate in clot formation.

Briefly the process of the present invention comprises pre-incubating the platelets in a special pre-incubation buffer formulated to maintain the cells biologically active, loading the cells with glucose, and lyophilizing the cells in a specific process dependent upon the specially formulated buffer such that lyophilized reconstituted cells are viable and have a high aggregation index.

BRIEF DESCRIPTION OF THE DRAWINGS

A more complete appreciation of the invention will be readily obtained by reference to the following Description of the Preferred Embodiments and the accompanying drawing, wherein.

DESCRIPTION OF THE PREFERRED EMBODIMENTS

Figure 1:
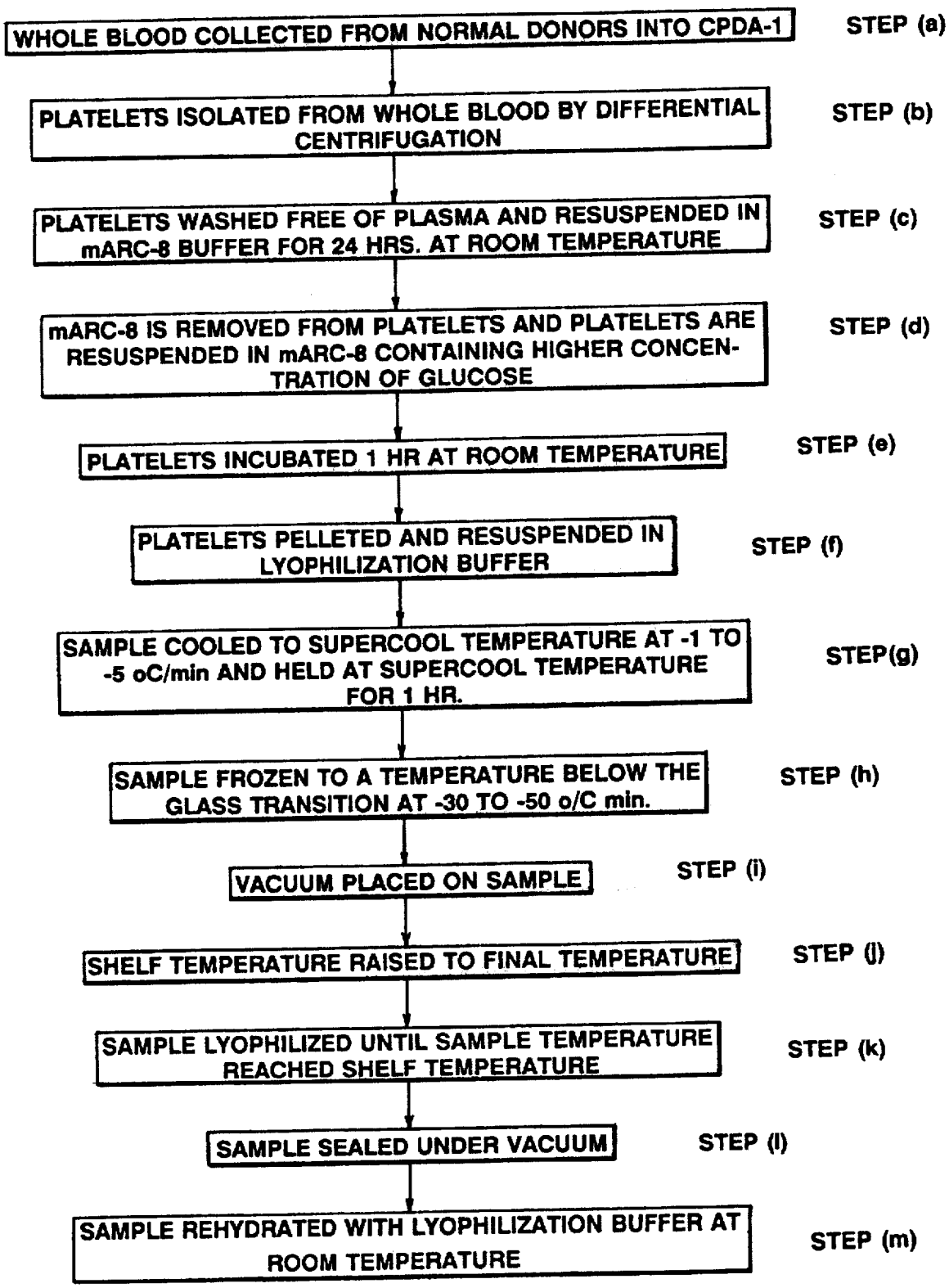
FIG. 1 is a flow chart illustrating an exemplary embodiment of the present invention.

While the present invention can be applied to hemosomes in general, it will be described in connection to platelets in particular. The complete content of the U.S. patent application Ser. No. 08/497,708 filed on Jun. 30, 1995, naming Spargo et al. as the inventors, and entitled Freeze-Dried Red Blood Cells and Platelets, is hereby incorporated by reference.

The process of the present invention includes pre-incubating the platelets in a pre-incubation buffer specially formulated to maintain the viability and function of the cells. The pre-incubation buffer of the present invention is a phosphate-phosphate-citrate buffer (double phosphate-citrate buffer, i.e., including a monobasic and a dibasic phosphate), or more simply a single phosphate-citrate buffer (including only one of a monobasic or dibasic phosphate). As used throughout the present specification and claims, the term phosphate-citrate buffer encompasses single- and double-phosphate-citrate buffers. The buffer is composed of a carbohydrate, typically a mono- or disaccharide such as glucose, at a concentration range of 10–1500 mM, preferably about 139 mM. Other buffer constituents can include: sodium citrate at a range of 1–50 mM, preferably at a concentration of about 33.3 mM; sodium phosphate, dibasic, at a range of 1–50 mM, preferably at a concentration of about 12.0 mM; sodium phosphate, monobasic, at a range of 1–15 mM, preferably at a concentration of about 2.9 mM; ammonium phosphate, at a range of 1–100 mM, preferably at a concentration of about 40.0 mM; adenine, at a range of 0–5 mM, preferably at a concentration of about 2.0 mM; and adenosine, at a range of 0–5 mM, preferably at a concentration of about 2.2 mM. The buffer can be prepared in distilled water, approximately 330 mOsmolar or isoosmotic, in a pH range of about 7.2–7.4. The cells are pre-incubated in the above-described buffer for about 1 hour to about 7 days, more preferably for about 12 to about 24 hours, most preferably about 20 hours. The temperature during pre-incubation is not particularly critical, although it can influence the required pre-incubation time. Usually, pre-incubation is conveniently performed at room temperature. Pre-incubation induces the Cl– shift. This Cl– shift results in significantly increased concentrations of ATP and 2,3-DPG. Increased concentrations of gycolytic intermediates such as ATP and 2,3-DPG appear to be critical to the restoration of platelet fuction, as well as platelet recovery and repair, upon rehydration.

After pre-incubation, the cells are loaded with carbohydrate by incubating platelets in a phosphate-citrate buffer similar to the pre-incubation buffer, but containing a higher carbohydrate concentration. Typically, the concentration of carbohydrate in the incubation buffer is many times higher than the concentration of glucose in the pre-incubation buffer. As is the case with the pre-incubation buffer, the carbohydrate in the incubation buffer may be a mono- or disaccharide, preferably glucose. Even though other sugars can be substituted for glucose including, maltose, trehalose and sucrose (disaccharides), glucose is preferred since it is thought to be easily transported or diffused across the membrane of the platelets and provide protection to the proteins in the system. The time and temperature for incubation may be adjust to allow for sufficient carbohydrate loading of the platelets. For example, incubation overnight at 4° C., or incubation for 1 hour at 25° C. has a similar effect; adequate time should be given for sufficient carbohydrate to be transported or to diffuse across the membrane. In the absence of this step, internal membrane integrity is lost and protein denaturation occurs. Preferably, the incubation temperature may be about 10°–37° C., more preferably about 20°–30° C., and most preferably about 25° C. These temperature ranges correspond to the same temperature ranges that are useful during the pre-incubation step. The concentration of carbohydrate in the loading buffer in the case of glucose, can be in the range of about 0.1 to 1.5M, preferably in the range of about 0.5 to 1.0M, and is most preferably in the range of about 0.75 to 1.0M.

Following incubation in the carbohydrate-loading buffer as described above, the platelets are resuspended in a lyophilization buffer. The lyophilization buffer has essentially the same as a buffer suitable for use as a pre-incubation buffer, but further includes a polymer and has a mono- or disaccaride concentratio of no greater than about 150 mM. The polymer can be present in a concentration of about 6 to about 40%, more preferably about 25–35%, and most preferably in a concentration of about 30%. Preferably, the polymer has an average molecular weight in the range of about 50–500 kDa, more preferably in the range of about 100 to about 300 kDa, most preferably about 150 kDa. Any polymer can be used which has the capability of forming a matrix that can support the platelets during lyophilization, and the collapse of the matrix can be controlled. Preferably, the polymer is non-toxic and capable of forming a hydrogel. For example, polymers can be selected from the group consisting of polyvinylpyrrolidone (PVP) and polyvinylpyrrolidone derivatives, dextran and dextran derivatives, and amino acid based polymers (e.g. proteins), starch and starch derivatives. Most preferred is the polymer hydroxyethyl starch (HES). One exemplary HES used in the examples of this specification included HES molecules with a range of molecular weights of 100–400 kDa and an average weight of about 150 kDa. A concentration of 20–30% (w/v) is preferred. HES provides a significant advantage in that it is readily transfusable whereas there is a requirement to reduce the concentration of PVP to 1 or 2 parts per billion before transfusion.

The term lyophilization is broadly defined as freezing a substance and then reducing the concentration of one of the solutes, namely water, by sublimation and desorption, to levels which will likely no longer support biological or chemical reactions. Usually, the drying step is accomplished in a high vacuum. However, with respect to the storage of cells and particularly platelets, the extent of drying is of critical importance in the ability of cells to withstand long-term storage at room temperature. In the method of the invention, cells may be lyophilized to a residual water content of 12 weight % or less, preferably less than 3%, and still be reconstituted to transfusable, therapeutically useful cells. Cells with about 3% by weight water content made in accordance with the present invention can be stored for up to about 5 years at room temperature, and at 4° C. for longer than about 10 years, and at –20° C. for even longer than 10 years, for e.g. about 25 years, without decomposition. This far exceeds the current American Association of Blood Bank standard for frozen or refrigerated platelets stored for 5 days at 25° C.

According to the process of the present invention, lyophilization is accomplished by slow cooling of the platelets suspended in the lyophilization buffer described above. Slow cooling is accomplished for example by placing the cells on the shelf of a temperature controlled shelf lyophilizer and slowly (typically about –1° to about –5° C./min and more often about –1° to about –2° C./min) reducing the temperature from room temperature to at supercooling temperature of about –5° to about –25° C. and more often to about –10° to about –15° C. After slow cooling, the suspension of platelets are incubated at that supercooling temperature for about one to two hours to form a supercooled suspension of platelets. After incubation at the supercooling temperature, the temperature is rapidly (about –20° to about –30° C./min) dropped to below the glass transition temperature (typically about –35) of the suspension to be lyophilized. Generally, this temperature ranges from about –40° to about –60° C. and is typically about –40° C. to about –55° C. and is most often about –45° C. to about 50° C. The glass transition temperature referenced here and in the appended claims is the glass transition temperature of the water in the system. This glass transition temperature does not change significantly during drying.

The suspension is held at this low temperature until the vacuum is reduced from 1 ATM to about 10 to 100 milliTorr (mT) and most often about 50–100 mT for primary drying. Generally, the rate at which the vacuum is applied is not critical and, in any event, is difficult to control. Typically, this primary drying step removes about 75 to about 80 weight percent of the water. The primary drying step typically takes from about 5 to about 20 hours, and more often about 5 to about 8 hours. Following primary drying, the shelf temperature is elevated to the secondary drying temperature which can be about –20° to +25° C., more preferably from about –20° to about 0° C., most preferably about –15° C., and held for the remainder of the drying phase under a vacuum of 10 to 100 mT, more preferably about 50–100 mT, most preferably 100 mT. When the sample temperature reaches the shelf temperature, the samples are sealed under vacuum and removed from the lyophilizer.

The lyophilization and drying of platelets described above is critical for the viability of the cells upon reconstitution. Previous lyophilization procedures, such as Goodrich (U.S. Pat. No. 5,213,814), failed to recognize the importance of the drying process and did not disclose such a process. Upon lyophilization according to the process of the present invention to a moisture content of less than about 15%, preferably less than about 12%, and more preferably less than about 3%, the lyophilized cells may be maintained under vacuum in vacuum-tight containers, or under nitrogen or other inert gas, at room temperature for extended periods of time in absence of or without significant degradation of, their desirable properties when reconstituted for use as transfusable cells. It is a particular advantage of the present invention that the lyophilized cells may be stored at room temperature for extended periods of time, thus obviating the need for low temperature refrigeration which is required for storing lyophilized platelets prepared by methods of the prior art.

It is a further advantage of the present invention that the lyophilized platelets may be reconstituted at normal temperatures, i.e. greater than about 17° C. up to about 37° C., which corresponds to normal human body temperature, and preferably at room temperature (about 22° C.). The reconstitution medium is preferably a solution comprising a non-toxic hydrogel-forming polymer, present in a concentration of about 20–30%, or a concentration such that a colligative force is present in order to prevent the structural collapse of cells. The reconstitution solution should further be buffered with a buffer solution to maintain a pH within the range of about 7.0 to 7.4. The most preferred reconstitution solution is a solution similar to the lyophilization solution described above namely, phosphate-citrate buffer with HES. Other polymers, including PVP and dextran, can substitute, partially or fully, for hydroxyethyl starch in the reconstitution solution. The lyophilized platelets can be reconstituted by mixing the cells with lyophilization buffer at room temperature and allowing the sample to fully rehydrate. The cells can be used for transfusion when fully hydrated, since all of the components present are biocompatible, or phosphate-citrate buffer can be added slowly until the HES concentration (w/v) is in the range of 0–10% if desirable. Alternatively, the cells can be pelleted and resuspended in 6% (w/v) hydroxyethyl starch in the phosphate-citrate buffer of the present invention or a phosphate-buffered saline solution.

A flow chart illustrating an exemplary sequence of steps for carrying out the present inventin is shown in FIG. 1. In step (a), whole blood is collected into a suitable buffer, such as CPDA-1, from normal donors. The platletes from this blood are isolated in step (b), typically by differential centrifugation. Then, the isolated platelets are washed free of plasma and resuspended in a pre-incubation buffer, such as mARC-8, for about 24, to induce the Cl− shift resulting in increased ATP (step (c)). In step (d), the pre-incubation buffer is removed from the platelets and the platelets are resuspended in an incubation buffer having a higher concentration of glucose, but a composition otherwise similar to a buffer suitable for use during the preincubation step. The platelets are incubated in this incubation buffer for about one hours, typically at room temperature for glucose loading (step (e)).

The incubated, glucose-loaded platelets are then pelleted and suspended in the lyophilization buffer (step (f)). Next, the suspension is supercooled, at a rate of about −1° to about −5° C./min and held at the supercooling temperature (most often about −10° to about −15° C.) (step (g)). After about one to two hours at supercooling temperatures (to allow equilibration of temperature throughout the suspension), the supercooled suspension is then frozen at a temperature below its glass transition temperature (step (g)). Typically, the supercooled suspension is frozen at about at a rate of −30° to about −50° C./min. The glass transition of the suspension in the present invention is usuallly about 35° C., due to the relatively low glucose concentration compared to prior art lyophilization buffers. The higher transition temperature of the buffered lyophilization suspension used in the present invention, and the fast freezing rate, essentially prevent the formation and growth of ice crystals.

Then, the frozen suspension is subjected to a vacuum (step (i)). The shelf temperature is then raised to the final lyophilization temperature. The final lyophilization temperature determines the water content of the final lyophilized product. For example, the water content of a platelets lyophilized at about −15° C. is usually about 10 to 12 weight percent. The water content of lyophilized plates can be reduced, down to a minimum of about 1 to 3 weight percent, by raising the final lyophilization temperature. After the suspension has reached the final lyophilization temperature (step (k)), the lyophilized product may be sealed under vacuum (step (l)). Then, before use, the lyophilized product is rehydrated in a lyophilization buffer, typically at about room temperature (step (m)).

As noted above, the process of the present invention provides a medium for the lyophilization and reconstitution of intact and biologically-active platelets. While the media of the invention are novel it will be understood that apparatus and related techniques are known by those with ordinary skill in the art for the lyophilization of various materials, and cells in particular, and only the specific temperatures and apparatus are employed herein. From this description, one of ordinary skill in the art will be capable of employing the novel media of the invention in the novel process for the freeze-drying and reconstitution of intact, viable platelets.

The present process includes centrifuging whole blood, removing plasma supernatant, resuspending the pellet in phosphate-citrate buffer of the present invention. This wash cycle can be repeated 2–3 times, then the packed cells are diluted in the phosphate-citrate buffer. Alternatively, commercially available packed cells may be used, which typically are prepared in CPDA-1 (commercial solution containing citrate, phosphate, dextrose and adenine) or CPDA-1-like solution, for example, Adsol.

Typically the reconstituted cells of the present invention have a high aggregation index and the cells retain their spherical morphology. Platelets prepared according to the present invention possess normal agglutination, are capable of degranulation and can participate in clot formation.

Having described the preferred embodiments of the present invention, the following examples describing different buffers and conditions are provided by way of illustration but are not intended to limit the invention in any way.

EXAMPLE 1

Sample Preparation

Platelets were isolated from fresh normal donor whole blood by differential centrifugation and stored in satellite bags at 25° C. with gentle mixing until used (within 96 hours). Platelets were then washed twice in 0.9% sodium chloride solution to remove serum and storage buffers. Buffer A was used to resuspend the platelets and consists of: 139 mM glucose, 33 mM citrate (Na salt), 12 mM $Na_2HPO_4$, 3 mM NaH$_2$PO$_4$, 40 mM (NH$_4$)$_2$HPO$_4$, 2 mM adenosine and 2 mM adenine. Platelets were stored at 25° C. for 24 hours in buffer A. Buffer A was removed following centrifugation and platelets were resuspended in buffer B containing: 33 mM citrate (Na salt), 12 mM Na$_2$HPO$_4$, 3 mM NaH$_2$PO$_4$, 40 mM (NH$_4$)$_2$HPO$_4$, 2 mM adenosine, 2 mM adenine, and 0.75M glucose and incubated at 25° C. for 1 hour. Following incubation, the buffer B was removed by centrifugation and the platelets were resuspended in a lyophilization buffer (buffer C) containing: 139 mM glucose, 33 mM citrate (Na salt), 12 mM Na$_2$HPO$_4$, 3 mM NaH$_2$PO$_4$, 40 mM (NH$_4$)$_2$HPO$_4$, 2 mM adenosine, 2 mM adenine, and 30% (w/v) hydroxyethyl starch.

Lyophilization

Platelets were aliquoted into serum vials at 10% total vial volume. Samples were placed on the shelf of a temperature controlled shelf lyophilizer. Samples were slowly reduced from room temperature (rt) to −15° C. and incubated for 1 hour. After equilibration at −15° C., the shelf temperature was rapidly dropped to −50° C. and held at that temperature until the vacuum reaches 100 mT. Following primary drying phase, the shelf temperature was elevated to −15° C. and held for the remainder of the drying cycle under a vacuum of 100 mT. When the sample temperature reaches the shelf temperature of −15° C., the samples were sealed under vacuum and removed from the lyophilizer.

Rehydration

Samples were rehydrated in a two step method. Following rehydration in buffer C, the hydroxyethyl starch concentration was reduced to between 6–10% (w/v) by the slow addition of buffer A. Platelets were isolated by centrifugation, resuspended and washed twice in buffer A.

This lyophilization and rehydration protocol resulted in the recovery of about 75–85% of the starting platelets in transfusable condition.

EXAMPLE 2

Sample Preparation

Platelets were isolated from fresh normal donor whole blood by differential centrifugation and stored in satellite bags at 25° C. with gentle mixing until used (within 96 hours). Platelets were then washed twice in 0.9% sodium chloride solution to remove serum and storage buffers. Platelets were resuspended in a buffer B containing: 33 mM citrate (Na salt), 12 mM Na$_2$HPO$_4$, 3 mM NaH$_2$PO$_4$, 40 mM (NH$_4$)$_2$HPO$_4$, 2 mM adenosine, 2 mM adenine, and 0.75M glucose and incubated at 25° C. for 1 hour. Following incubation, the buffer B was removed by centrifugation and the platelets were resuspended in a lyophilization buffer (buffer C) containing: 139 mM glucose, 33 mM citrate (Na salt), 12 mM Na$_2$HPO$_4$, 3 mM NaH$_2$PO$_4$, 40 mM (NH$_4$)$_2$HPO$_4$, 2 mM adenosine, 2 mM adenine, and 30% (w/v) hydroxyethyl starch.

Lyophilization

Platelets were aliquoted into serum vials at 10% total vial volume. Samples were placed on the shelf of a temperature controlled shelf lyophilizer. Samples were slowly reduced from room temperature (rt) to −15° C. and incubated for 1 hour. After equilibration at −15° C., the shelf temperature was rapidly dropped to −50° C. and held at that temperature until the vacuum reaches 100 mT. Following primary drying phase, the shelf temperature was elevated to −15° C. and held for the remainder of the drying cycle under a vacuum of 100 mT. When the sample temperature reached the shelf temperature of −15° C., the samples were sealed under vacuum and removed from the lyophilizer.

Rehydration

Samples were rehydrated in a two step method using buffer C. Following rehydration, the hydroxyethyl starch concentration was reduced to between 6–10% (w/v) by the slow addition of buffer A. Platelets were isolated by centrifugation, resuspended and washed twice in buffer A.

Typically, this protocol resulted in about 70–75% of the starting platelets in condition for transfusion.

EXAMPLE 3

Sample Preparation

Platelets were isolated from fresh normal donor whole blood by differential centrifugation and stored in satellite bags at 25° C. with gentle mixing until used (within 96 hours). Platelets were then washed twice in 0.9% sodium chloride solution to remove serum and storage buffers. Platelets were resuspended in a buffer (buffer C) containing: 139 mM glucose, 33 mM citrate (Na salt), 12 mM Na$_2$HPO$_4$, 3 mM NaH$_2$PO$_4$, 40 mM (NH$_4$)$_2$HPO$_4$, 2 mM adenosine, 2 mM adenine, and 30% (w/v) hydroxyethyl starch.

Lyophilization

Platelets were aliquoted into serum vials at 10% total vial volume. Samples were placed on the shelf of a temperature controlled shelf lyophilizer. Samples were slowly reduced from room temperature (rt) to −15° C. and incubated for 1 hour. After equilibration at −15° C., the shelf temperature is rapidly dropped to −50° C. and held at that temperature until the vacuum reached 100 mT. Following primary drying phase, the shelf temperature was elevated to −15° C. and held for the remainder of the drying cycle under a vacuum of 100 mT. When the sample temperature reached the shelf temperature of −15° C., the samples were sealed under vacuum and removed from the lyophilizer.

Rehydration

Samples were rehydrated in a two step method using buffer C. Following rehydration, the hydroxyethyl starch concentration was reduced to between 6–10% (w/v) by the slow addition of buffer A. Platelets were isolated by centrifugation, resuspended and washed twice in buffer A.

This protocol resulted in about 50% of the starting platelets in transfusably useful condition.

Obviously, many modifications and variations of the present invention are possible in light of the above teachings. It is therefore to be understood that, within the scope of the appended claims, the invention may be practiced otherwise than as specifically described.

What is claimed is:

1. A process for storing a composition consisting essentially of platelets comprising the steps of:
   preincubating the platelets in a preincubation buffer comprising carbohydrate selected from the group consisting of monosaccharides and disaccharides, in a concentration of about 10 mM to 150 mM which is capable of inducing a Cl⁻ shift which results in increased concentrations of ATP and 2,3-DPG in the platelets;
   loading the platelets with carbohydrate by incubating the platelets in a second buffer having a higher concentration of carbohydrate than the preincubation buffer and comprising carbohydrate selected from the group consisting of monosaccharides and disaccharides, in a concentration of about 100–1500 mM for a time sufficient to increase the carbohydrate concentration of the platelets, thus forming carbohydrate-loaded platelets;

suspending the carbohydrate-loaded platelets in a lyophilization buffer comprising a carbohydrate selected from the group consisting of monosaccharides and disaccharides, in a concentration of about 10 mM to 150 mM, and a biocompatible polymer having a molecular weight of about 50–500 kDa, in a concentration of about 10–30% w/v;

supercooling the suspended platelets to a temperature of about −5° to about −25° C. and maintaining the temperature for a time sufficient to allow temperature equilibration of the suspension, thus forming a supercooled suspension of platelets;

cooling said supercooled suspension of platelets to below its glass transition temperature, thus forming a frozen suspension of platelets;

removing water from said frozen suspension of platelets by placing said frozen suspension under 10–100 mTorr of pressure while maintaining the suspension below its glass transition temperature, thus forming a dehydrated platelet composition;

raising the temperature of the dehydrated platelet composition to about −5° to −25° C. while maintaining 10–100 mTorr of pressure, thus forming lyophilized platelets having a moisture content of less than about 15% by weight.

2. A process for storing a composition consisting essentially of platelets comprising the steps of:

loading the platelets with carbohydrate by incubating the platelets in an incubation buffer comprising carbohydrate selected from the group consisting of monosaccharides and disaccharides, in a concentration of about 100 mM to 1500 mM which is capable of inducing a Cl⁻ shift which results in increased concentrations of ATP and 2,3-DPG in the platelets and thereby loading the platelets with carbohydrate, thus forming carbohydrate-loaded platelets;

suspending the carbohydrate-loaded platelets in a lyophilization buffer comprising a carbohydrate selected from the group consisting of monosaccharides and disaccharides, in a concentration of about 10 mM to 150 mM, and a biocompatible polymer having a molecular weight of about 50–500 kDa, in a concentration of about 10–30% w/v;

supercooling the suspended platelets to a temperature of about −5° to about −25° C. and maintaining the temperature for a time sufficient to allow temperature equilibration of the suspension, thus forming a supercooled suspension of platelets;

cooling said supercooled suspension of platelets to below its glass transition temperature, thus forming a frozen suspension of platelets;

removing water from said frozen suspension of platelets by placing said frozen suspension under 10–100 mTorr of pressure while maintaining the suspension below its glass transition temperature, thus forming a dehydrated platelet composition;

raising the temperature of the dehydrated platelet composition to about −5° to −25° C. while maintaining 10–100 mTorr of pressure, thus forming lyophilized platelets having a moisture content of less than about 15% by weight.

3. The process of claim 1 or 2, wherein the buffer of said loading step further comprises phosphate and citrate.

4. The process of claim 1 or 2, wherein the carbohydrate is glucose.

5. The process of claim 1 or 2, wherein the supercooling step is about −5° to about −15° C.

6. The process of claim 1 or 2, wherein the supercooling step is performed at a rate of about −1° to about −5° C. per minute.

7. The method of claim 1 or 2, wherein said biocompatible polymer is a hydrogel-forming polymer.

8. The method of claim 1, wherein said biocompatible polymer has an average molecular weight of 100–500 kDa.

9. The method of claim 1 or 2, wherein said biocompatible polymer is hydroxyethyl starch.

10. The method of claim 9, wherein said hydroxyethyl starch has an average molecular weight of 50–500 kDa.

11. The process of claim 1, wherein the preincubation buffer farther comprises phosphate and citrate.

12. The process of claim 10, wherein the citrate is sodium citrate in a concentration of about 1–50 mM and the phosphate is sodium phosphate dibasic in a concentration of about 1–50 mM and sodium monobasic in a concentration of about 1–100 mM and ammonium phosphate in a concentration of about 1–100 mM, and the preincubation buffer further comprises adenine in a concentration of about 0–5 mM and adenosine in a concentration of about 0–5 mM.

13. The process of claim 1 or 2, wherein said lyophilization buffer further comprises sodium citrate in a concentration of about 1–50 mM, sodium phosphate dibasic in a concentration of about 1–50 mM, sodium phosphate monobasic in a concentration of about 1–15 mM, ammonium phosphate in a concentration of about 1–100 mM, adenine in a concentration of about 0–5 mM, and adenosine in a concentration of about 0–5 mM.

14. The process of claim 1 or 2 further comprising the step of rehydrating the lyophilized platelets in a rehydration buffer comprising a carbohydrate selected from the group consisting of monosaccharides and disaccharides, in a concentration of about 10 mM to 150 mM, and a biocompatible polymer having a molecular weight of about 50–500 kDa, in a concentration of about 10–30% w/v, at a temperature of about 15°–50° C., thus forming a suspension of rehydrated platelets.

15. The process of claim 14, further comprising the step of diluting the concentration of said polymer in said suspension of rehydrated platelets to a concentration of about 6% w/v to about 10% w/v.

16. The process of claim 1 or 2, wherein said step of removing water removes about 75 to about 80 weight percent of the water in said frozen suspension of platelets.

* * * * *